United States Patent [19]

Miller

[11] Patent Number: 5,066,785

[45] Date of Patent: *Nov. 19, 1991

[54] CARBOXYL TERMINAL PEPTIDE AND PROTEIN SEQUENCING

[75] Inventor: Chad G. Miller, Los Angeles, Calif.

[73] Assignee: City of Hope, Duarte, Calif.

[*] Notice: The portion of the term of this patent subsequent to Jun. 19, 2007 has been disclaimed.

[21] Appl. No.: 311,966

[22] Filed: Feb. 17, 1989

Related U.S. Application Data

[63] Continuation-in-part of Ser. No. 271,328, Nov. 15, 1988, Pat. No. 4,935,494.

[51] Int. Cl.$^5$ ................................................ C07K 1/10
[52] U.S. Cl. ...................................... 530/345; 436/89
[58] Field of Search ........................... 530/345; 436/89

[56] References Cited

U.S. PATENT DOCUMENTS 4,837,165 6/1989 Hawke .................................. 436/89

OTHER PUBLICATIONS

Ueda et al., Macromolecules (1988), 21, pp. 19–24.
Ueda et al., Polymer Journal, vol. 19 (1987), pp. 673–679.

Primary Examiner—Howard E. Schain
Assistant Examiner—Choon Koh
Attorney, Agent, or Firm—Edward S. Irons

[57] ABSTRACT

Methodology is described for the carboxyl-terminal sequencing of proteins and peptides using novel coupling reagents.

10 Claims, 7 Drawing Sheets

CARBOXYL TERMINAL PEPTIDE AND PROTEIN SEQUENCING

This application is a continuation-in-part of Ser. No. 271,328 filed Nov. 15, 1988, now U.S. Pat. No. 4,935,494.

FIELD OF THE INVENTION

This invention relates to the carboxyl-terminal (C-terminal) amino acid sequence analysis of peptides and proteins. More particularly, the invention relates to novel C-terminal coupling reagents, to the methodology for using these reagents, and to the novel coupling reaction products produced.

BACKGROUND OF THE INVENTION

Known C-terminal sequencing methodologies are enzymatic physical or chemical. The enzymatic approach is basically a time-course carboxypeptidase procedure. It is limited by differential hydrolysis rates of the involved peptide bonds and by potential unaccessibility of the COOH carboxyl terminus in proteins. The approach may yield the correct amino acids but in the wrong order and may not extend to more than three to five amino acids.

Physical approaches include mass spectrometry and nuclear magnetic resonance (NMR) and are most suitable for small peptides. Fast atom bombardment--Mass Spectrometry (FAB/MS) sensitivity for determining an entire peptide sequence is in the range of 1–10 nmol and is limited to expensive multisector instruments. Micromolar samples are required for NMR analysis.

Four chemical methods of some interest are known. In 1978 Parkam and Loudon reported a method in which the carboxyamido peptide derivative is treated with bis(1,1 trifluoroacetoxy)iodobenzene to yield a derivative of the amino acid. Free COOH groups were treated with bis-p-nitrophenylphosphoryl azide to generate the carboxyamido derivative through a Curtius rearrangement.[1]
[1] Parham, M.E. and Loudon G.M. *Biochem. Biophys. Res. Commun.* 80:1;7 (1978).

Loudon and coworkers presented another version of the method which entailed reaction of the COOH terminus with pivaloylhydroxyl amine in the presence of carbodimide to effect a Lossen rearrangement. This method failed to degrade aspartic and glutamine residues.[2]
[2] Miller, m.J and Loudon, G.M., *J. Am. Chem. Soc.* 97:5296 (1975); Miller, M.J., et al., *J. Org. Chem.* 42:1750 (1977).

The method reported by Stark[3] releases the COOH-terminal amino acid as a thiohydantoin. It entails activation of the COOH group with acetic anhydride, followed by reaction with ammonium thiocyanate and cleavage by acid or base hydrolysis to release the thiohydantoin from the peptide chain.
[3] Stark, G.R. *Biochemistry* 8:4735 (1968); Stark, G.R. in "Methods in Enzymology", Vol. 25, p. 369, Academic Press, New York, N.Y. (1972).

Hawke reported a modification of the Stark chemistry in which trimethylsilylisothiocyanate is utilized as the coupling reagent.[4]
[4] Hawke, et al. *Analytical Biochemistry* 166:298-307 (1987).

Notwithstanding these procedures, there is a continuing substantial need for a generally applicable chemical method for C-terminal sequencing. Such a method would have particular value with respect to, among other things, sequencing N-terminal blocked polypeptides and proteins, verifying the primary protein structures predicted from DNA sequences, providing practical detection of post translational processing of gene products from known codon sequences, and as an aid in the design of oligonucleotide cDNA or gene bank probes.

SUMMARY OF THE INVENTION

This invention provides practical C-terminal peptide sequencing methodology utilizing novel phosphoryl amide preferably phosphoryl thioamide coupling reagents which yield arylhydantoin, arylthiohydantoin or aryliminohydantoin cleavage products. The peptide may be preactivated with acetic anhydride and acetic acid. As compared with the prior art chemical procedures yielding thiohydantoin, aldehyde or iminohydantoin cleavage products, elaboration of the aryl ring imparts enhanced molar absorptivity to the cleavage product molecule and hence greater sensitivity to detection either in the UV or fluorescent spectra. Practical C-terminal sequencing of nanomole and sub-nanomole peptide and protein samples with positive identification, for example, by capillary electrophoresis, of released amino acids is facilitated.

DESCRIPTION OF THE PREFERRED EMBODIMENTS

The Coupling Reagents

The novel phosphoryl amide coupling reagents of this invention are of the schematic Formula I:

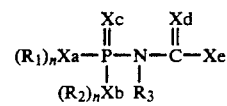

in which Xa and Xb are O (oxygen), S (sulfur) or N (nitrogen)

$R_1$ and $R_2$ are H, or any alkyl or aryl radical having not more than about 10 carbon atoms, n is 1 when Xa and Xb are O or S;

n is 2 when Xa or Xb is N when Xa and Xb are both N $(R_1)_n Xa$ and $(R_2)_n Xb$ may be included in an acylic amine or a nitrogen heterocycle;

$R_4$ is an alkyl or aryl radical having not more than about 10 carbon atoms;

Xc is O or S

Xd is O, S or $NR_4$ wherein $R_4$ is H or any alkyl or aryl radical having not more than about 10 carbon atoms Xe is $OR_5$, $SR_5$ or $N(R_5)_2$ wherein $R_5$ is an alkyl or aryl radical having not more than about 12 carbon atoms, and in which

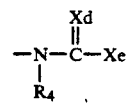

may be included in a ring system.

The alkyl or aryl groups which may constitute $R_1$, $R_2$, $R_3$, or $R_4$ perferably have from 3 to about 6 carbon atoms. The alkyl groups may be straight or branch chain. The aryl groups may be substituted or unsubstituted phenyl or napthyl groups.

Representative phosphoryl amide coupling reagents of this invention are represented by the compounds of formulas A, B, C, and D in which "PhO" is

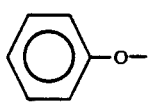

and Z is O or S:

A. 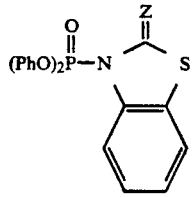

B. 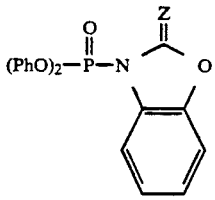

C. 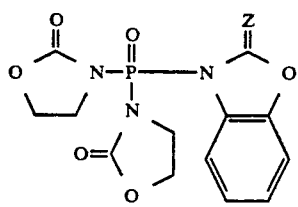

D. 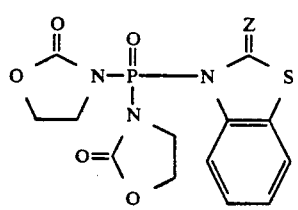

Additional phosphoryl amide coupling agents of the invention include the compounds of formulas E, F, and G:

E. 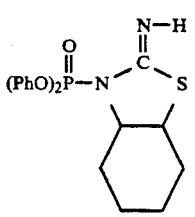

F. 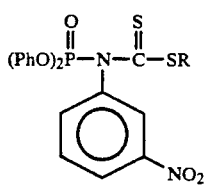

G. 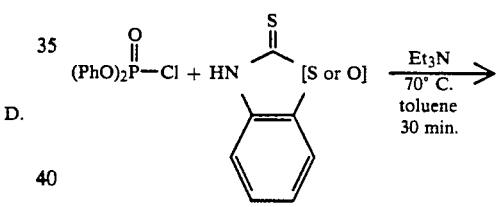

Any of the coupling reagents can be utilized as the free amides preferably after preactivation of the C-terminal acid of the peptide samples with acetic acid and acetic anhydride.

SYNTHESIS OF THE COUPLING AGENTS

The coupling agents of this invention may be synthesized by chemistry related to that used to produce certain known phosphoryl(thio)amide compounds.[5] For example a phosphorylating agent such as $$(PhO)_2-\overset{O}{\underset{\|}{P}}-Cl$$

may be reacted with a mercaptobenzothiazole, aminobenzothiazole, mercaptobenzoxazole or N, N' trisubstituted thiourea such as pyridyl, methyl, N'-m-nitrophenyl thiourea, to produce the compounds of formulas A through H. The reaction proceeds in the manner illustrated by Equation 1:

1.
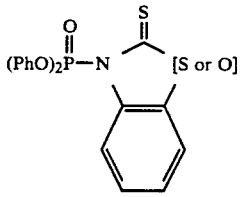

[5] See, e.g., Kirsanov, A.V., and Levchenko, E.S. *Zhur. Obsschcheu Khim*, 26:2285-2289 (1956); *ibid* 22:673-676 (1956); *ibid*. 31:210-216 (1961); Kulka, M., *Can. J. Chem.* 37:525-528 (1959); Ballester-Rodes, M. and Palomo-Coll, A.L., *Synthetic Communications*, 14:515-520 (1984) and Kuneida, T., Abe, Y., Higuchi, T., and Hirobe, M. *Tetrahedron Letters*, 22:1257-1258 (1981).

The synthesis is appropriately accomplished at a temperature from about 20° C. to about 100° C. in an inert solvent in the presence of an amine. Appropriate solvents include dimethyl formamide, dichloromethane, acetonitrile, saturated aliphatic hydrocarbons having from about 5 to about 10 carbon atoms, aromatic hydrocarbons including benzene, toluene, xylene and mesitylene. Tertiary amines which do not react with the phosphorylating agent under the reaction conditions may be utilized. Trialkyl amines having from 1 to about 5 carbon atom alkyl groups are appropriate. Triethylamine is preferred. The reaction time may range from about 15 min. to about 60 min. The reaction is normally complete in about 30 min.

EXAMPLE I

Synthesis of Compound of Formula A 1 millimole of 2-mercaptobenzothiazole was dissolved in 0.5 ml of toluene followed by the addition of 1 millimole of triethylamine. This solution was added to a solution of 1 millimole of diphenylchlorophosphate in 1 ml of toluene heated at 70° C. The mixture was reacted for two hours at 70° C., allowed to cool, filtered, and the filtrate evaporated to yield a yellow solid analyzed for the compound of Formula A. Calculated exact mass of the Formula A compound is 400.0231 atomic mass units (amu). The average of several exact mass determinations of the compound produced in Example I as determined by FAB-MS was 400.0256 amu. A yield of 40% to 50% of theoretical was obtained.

EXAMPLE II

Synthesis of Compound of Formula B

This example illustrates the synthesis of the compound of Formula B. 1 millimole of 2-mercaptobenzoxazole was dissolved in 0.5 ml toluene followed by the addition of 1 millimole of triethylamine. This solution was added to a solution of 1 millimole of diphenyldiohorophosphate in 1 ml of toluene heated to 70° C. and the mixture was reaoted for 30 minutes. The reaction mixture was filtered and the filtrate evaporated leaving a white solid. The yield of Formula B compound from a plurality of such reactions of ranged from 20% to 50% of theoretical. The calculated exact mass for the compound of Formula B is 384.0460 amu. The average of several exact mass determinations of the product of Example II as determined by FAB-MS is 384.0415 amu.

Formula C and D compounds are produced in like manner by reacting 2-mercaptobenzothiazole or 2-mercaptobenzoxazole with

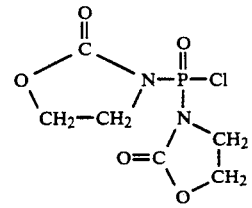

The Coupling Reaction

The reaction of dansylnorvaline with the compound of Formula A provides a model for carboxylic acid activation as the first coupling step require in the C-terminal sequencing methodology of this invention.

As illustrated by Equation 2, in a model reaction the piperidine salt of dansylnorvaline is utilized to permit direct reaction of an amino acid carboxylate with the compound of Formula A.

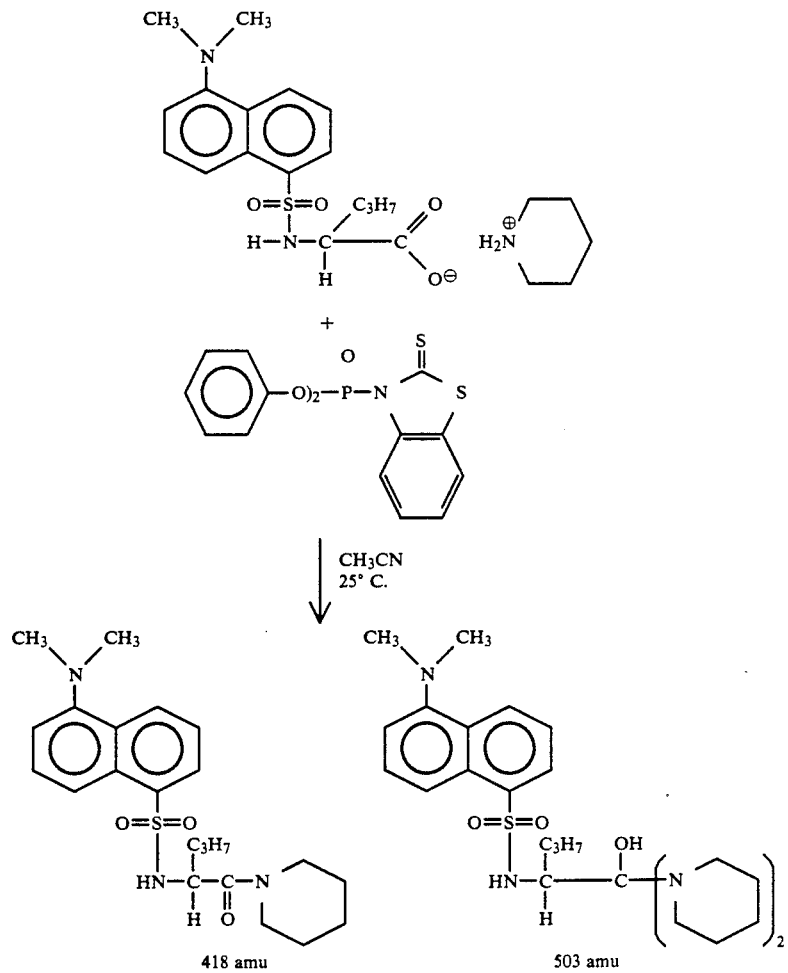

Under the conditions shown by Equation 2, the reaction proceeds at 25° C. in an acetonitrile solvent. Molecular ions of 418 and 503 amu are detected by FAB-MS after 2 minutes reaction time and persist after three hours.

These two products are consistent with the carboxyl activation of the amino acid by the compound of Formula A to provide the intermediate activated carboxylate:

which decomposes or reacts with the initially present nucleophilic amine piperidine.

Generalized coupling reactions involving the Formula A compound and the subsequent cyclization reaction are illustrated by Equations 3a and 3b. A peptide is depicted from the amino-terminal residue ($R^1$ through $R^3$) up to the carboxy terminal residue which is labelled as $R^3$, although peptides or proteins of any length may be considered.

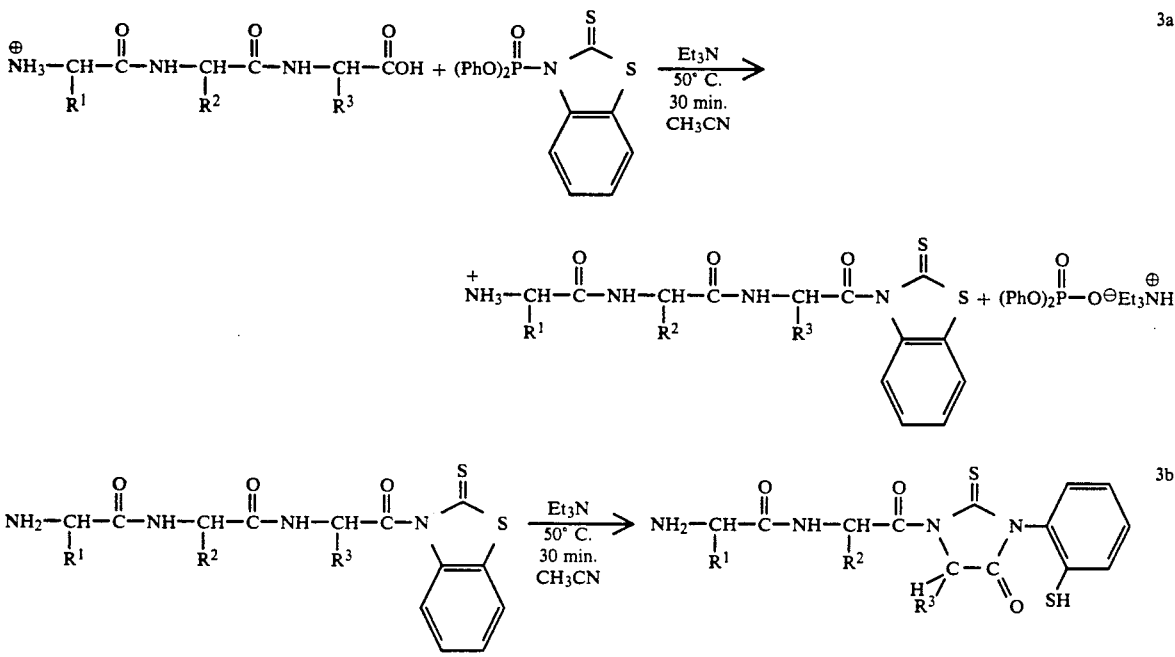

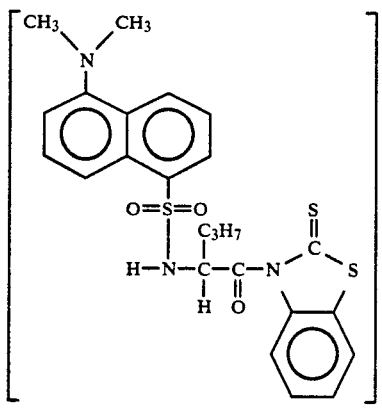

EXAMPLE III

This example illustrates a peptide coupling reaction with the use of the amino-terminally blocked tripeptide N-dansyltriglycine (DG3).

Figure 1:
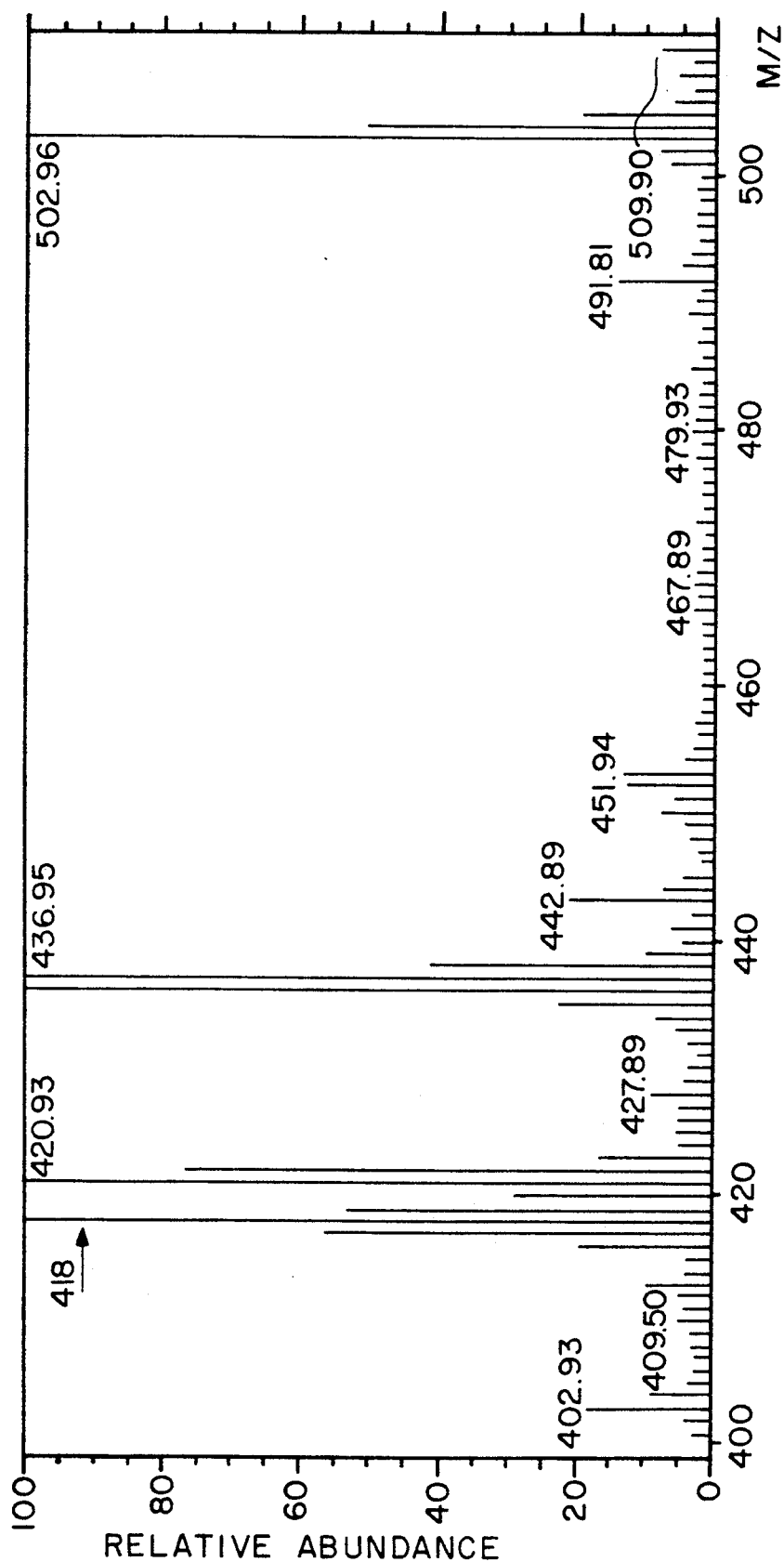
FIG. 1 is a FAB mass spectrum evidencing a molecular ion of 503 amu after the Equation 2 reaction had proceeded for three hours.
Figure 2:
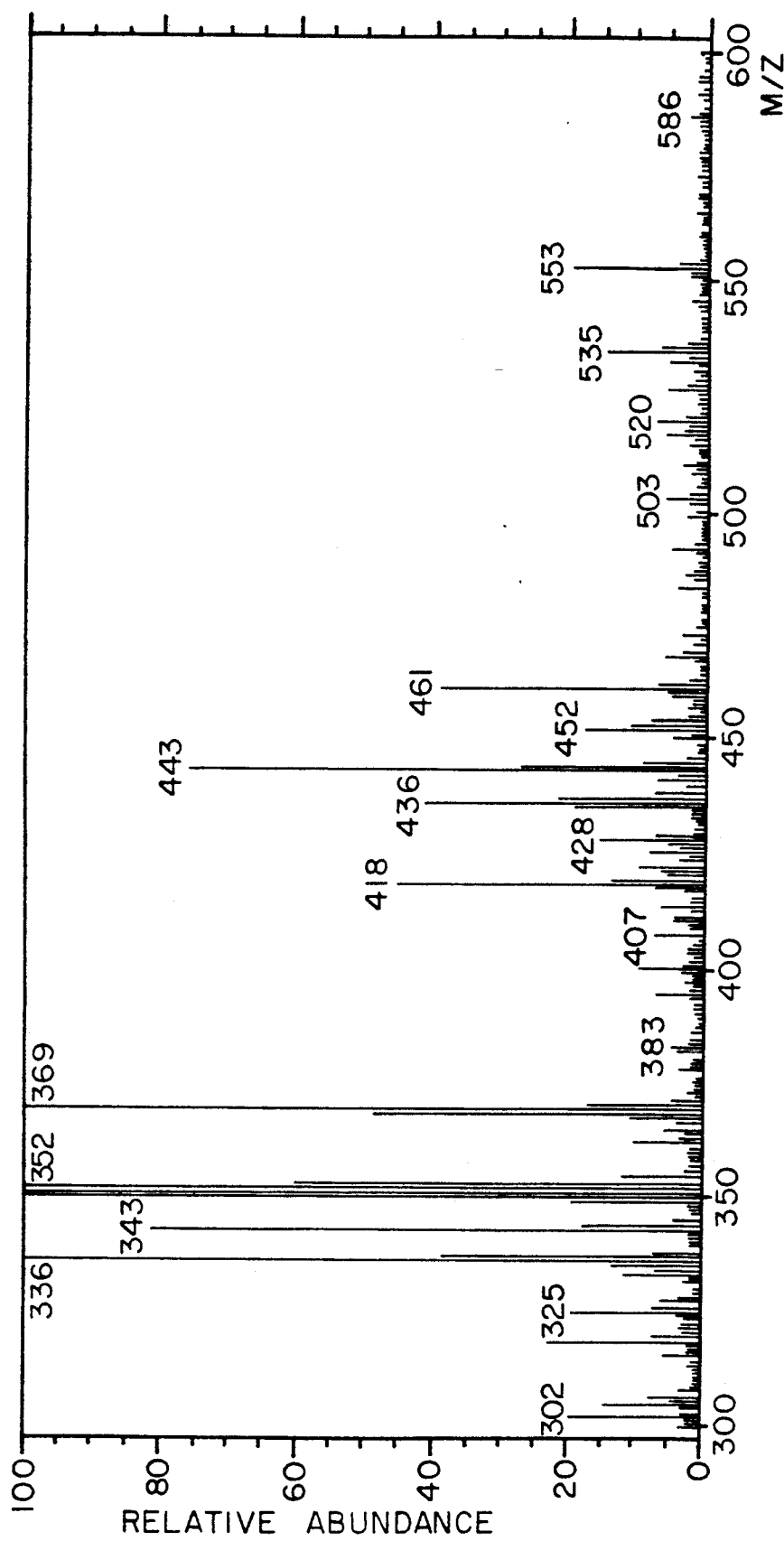
FIG. 2 is a FAB mass spectrum evidenoing a molecular ion of 418 amu after the Equation 2 reaction had proceeded for two minutes.
Figure 3:
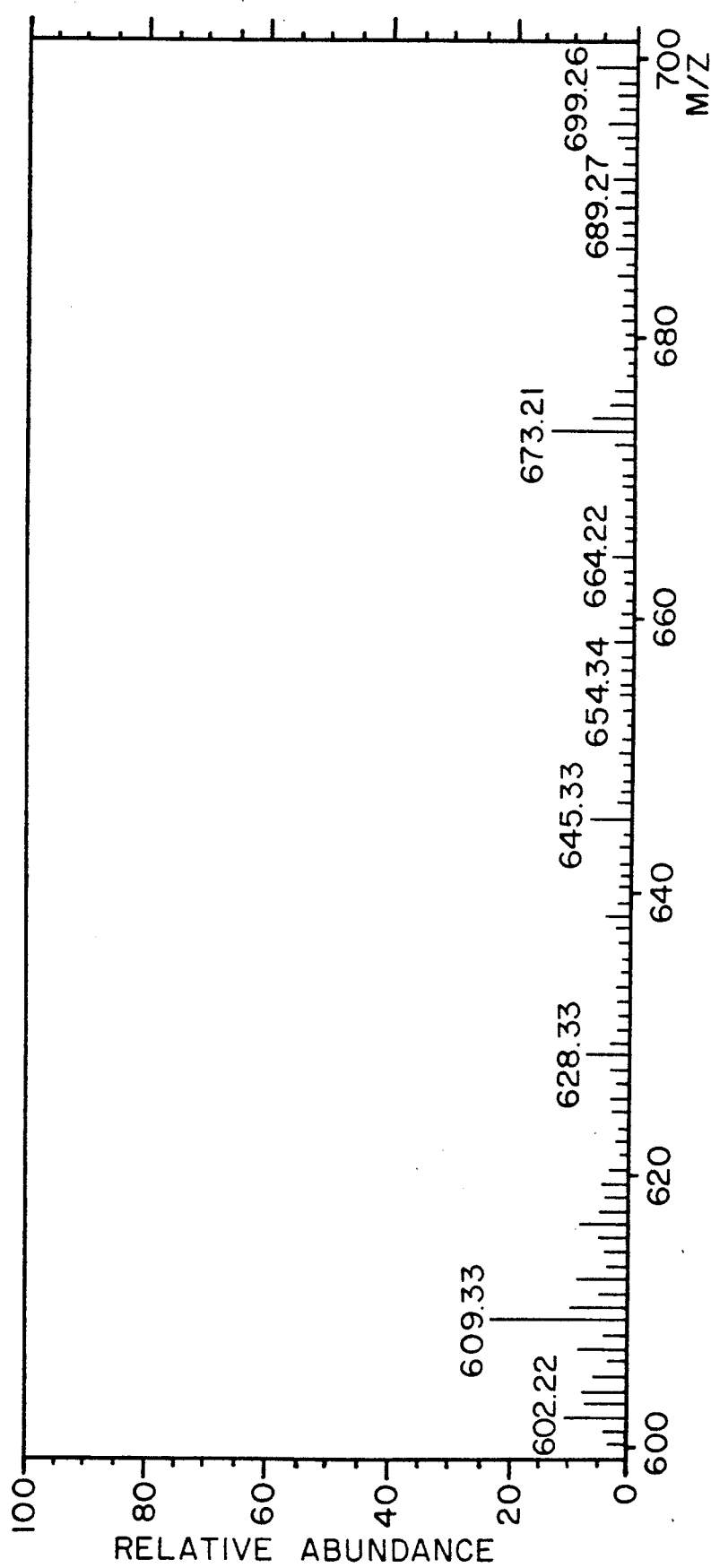

About 20 nanomoles of N-dansyltriglycine, dissolved in 20 μl (microliters) of acetonitrile, was reacted with about 10-20 μmoles of compound A in 15 μmoles of triethylamine. The reaction was performed several times at about 25° C. over time courses of from one to 24 hours. FAB-MS data show a molecular ion of 673 amu (see FIG. 3) which is consistent with the triethylamine (TEA) salt of the coupled peptide molecular ion formed pursuant to Equation 4:

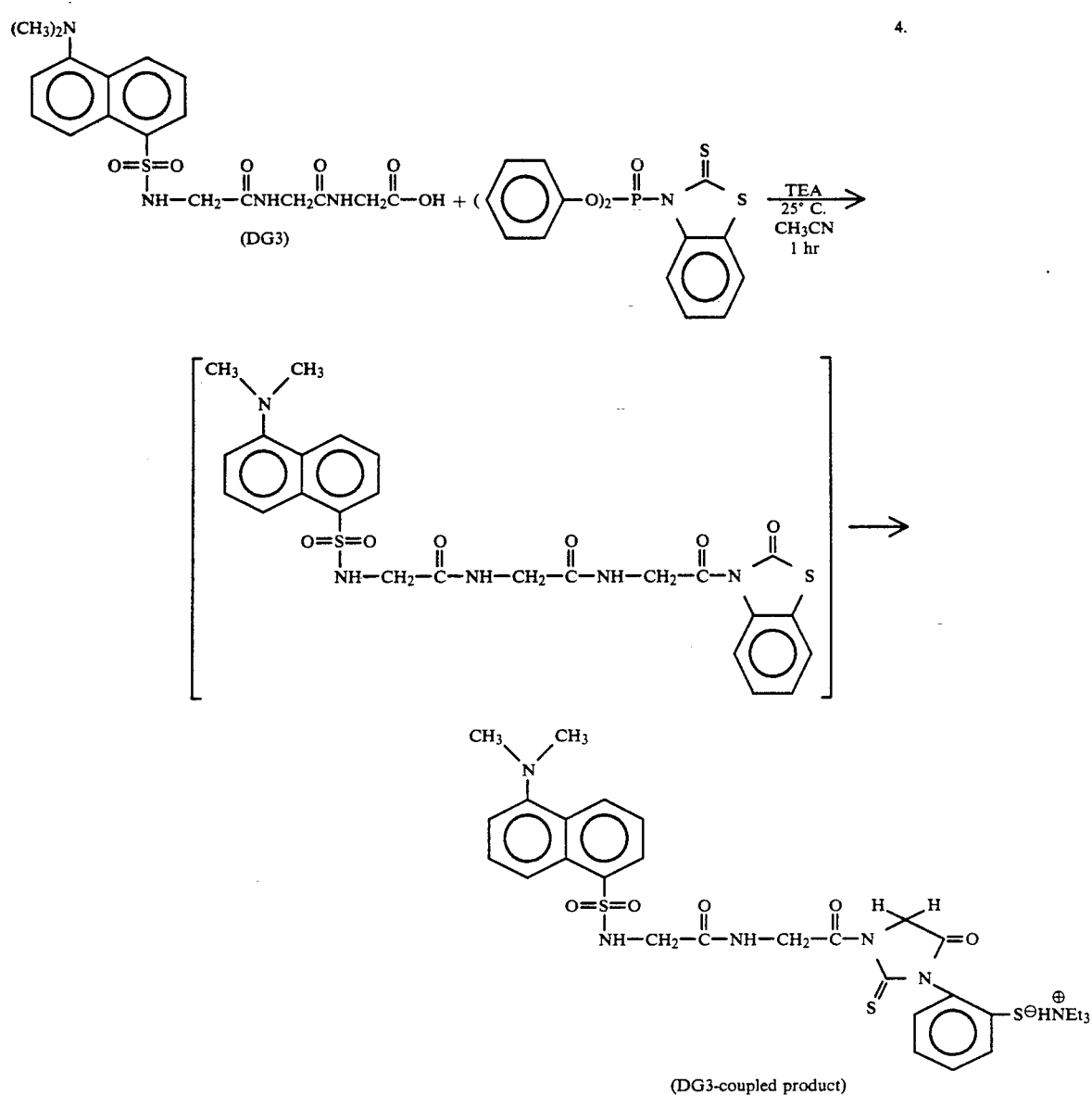
This structure indicates the cyclization of the intermediate coupled peptide, i.e.,
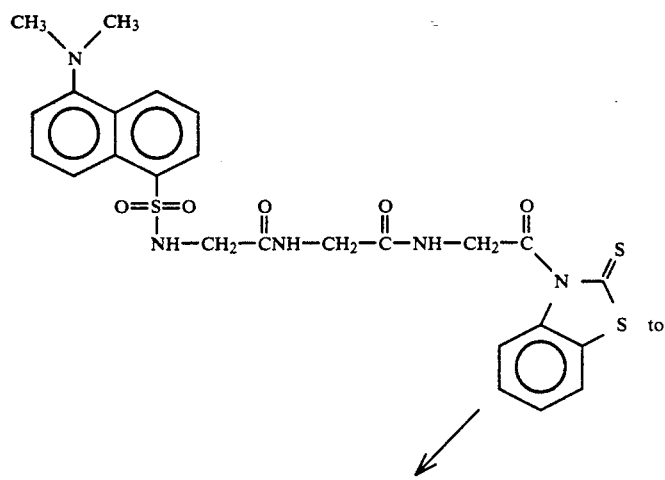

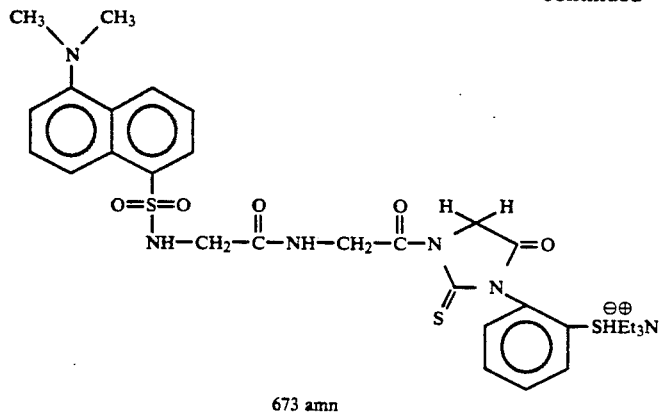

673 amu

The cyclized product exists as its triethylamine salt and gives rise to the 673 amu molecular ion.

Figure 4:
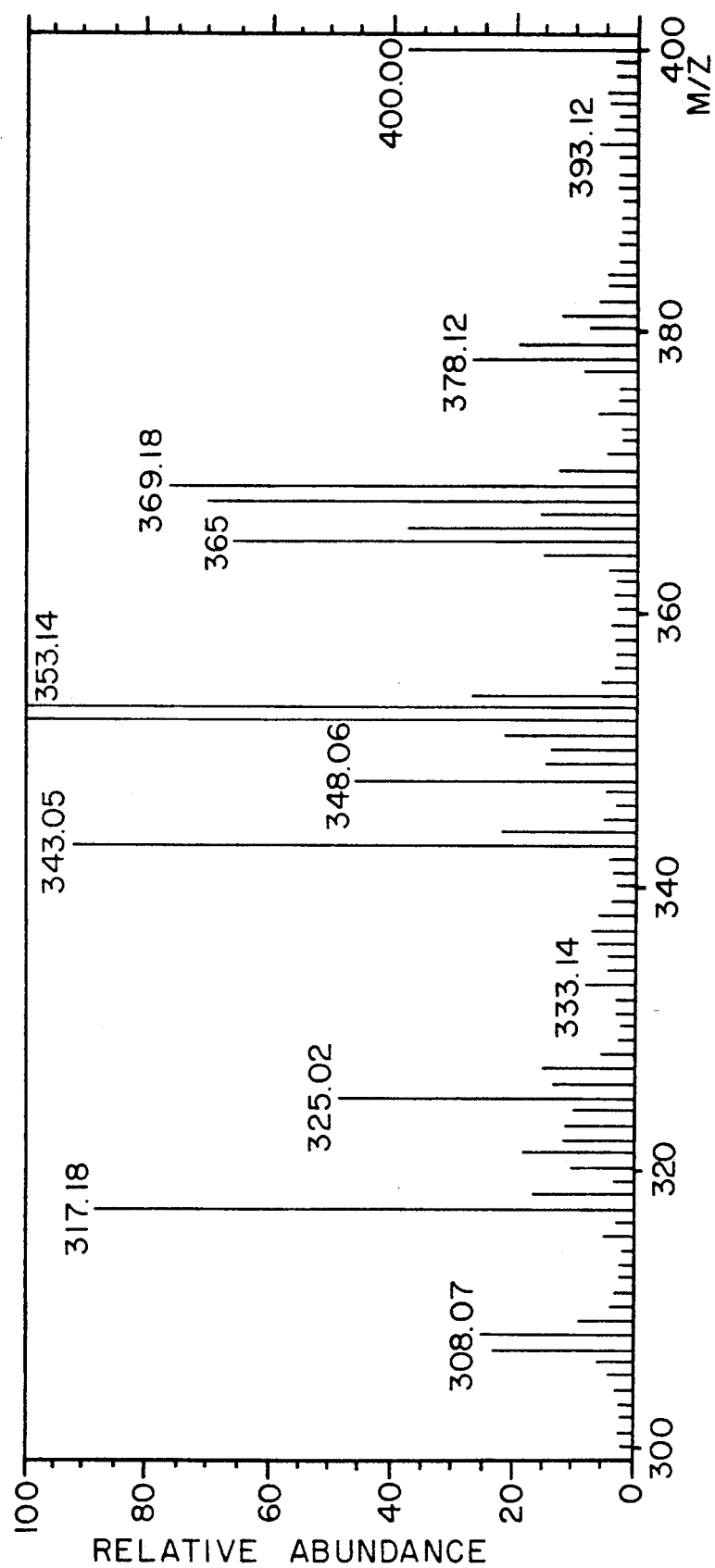

A molecular ion of 348 amu (FIG. 4) is consistent with a fragmention

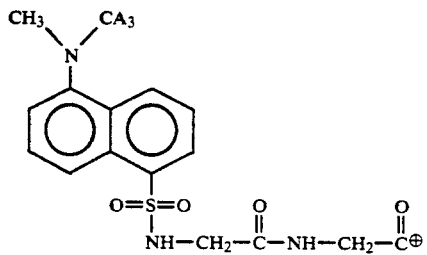

of the cyclized product.

A FAB mass spectral ion detected at 571 amu, consistent with the parent molecular ion calculated for the coupled peptide (not as its triethylamine salt), was found when N-dansyltriglycine was reacted with a 5,000-fold molar excess of compound A and triethylamine for 30 minute at 50° C. and subsequent brief (1 to 2 minute) exposure to a dilute aqueous sodium hydroxide solution (0.1 N).

Coupling utilizing the novel reagents of this invention, is facilitated by immobilization, preferably covalent, of the protein in known manner to a solid support. Preferred solid supports include derivatized polyvinyldifluoride membranes (Millipore Immobllon) and inert carriers such as polystyrene beads and controlled pore glass (CPG). Immobilization through nucleophilic groups, e.g., protein lysine residues is preferred. In this way the requirement for pretreatment of the protein with an amino-blocking reagent such as acetic anhydride may be avoided.

The coupling reaction may be accomplished in the presence of various bases. Triethyl amine is preferred. Other amines which may be utilized include trialkyl amines in which the alkyl groups have from one to about 5 carbon atoms, aryl amines such as pyridine or the Aldrich proton sponge.

The coupling reaction rate is a function of reaction temperature. A preferred temperature range is from about 25° C. to about 60° C. Any appropriate solvent may be utilized. Acetonitrile is preferred. N,N-dimethylformamide and dimethylsulfoxide are useful solvents.

EXAMPLE IV

This example illustrates, by comparative experiments, the acetic anhydride-acetic acid preactivation of a peptide to be sequenced.

Figure 5:
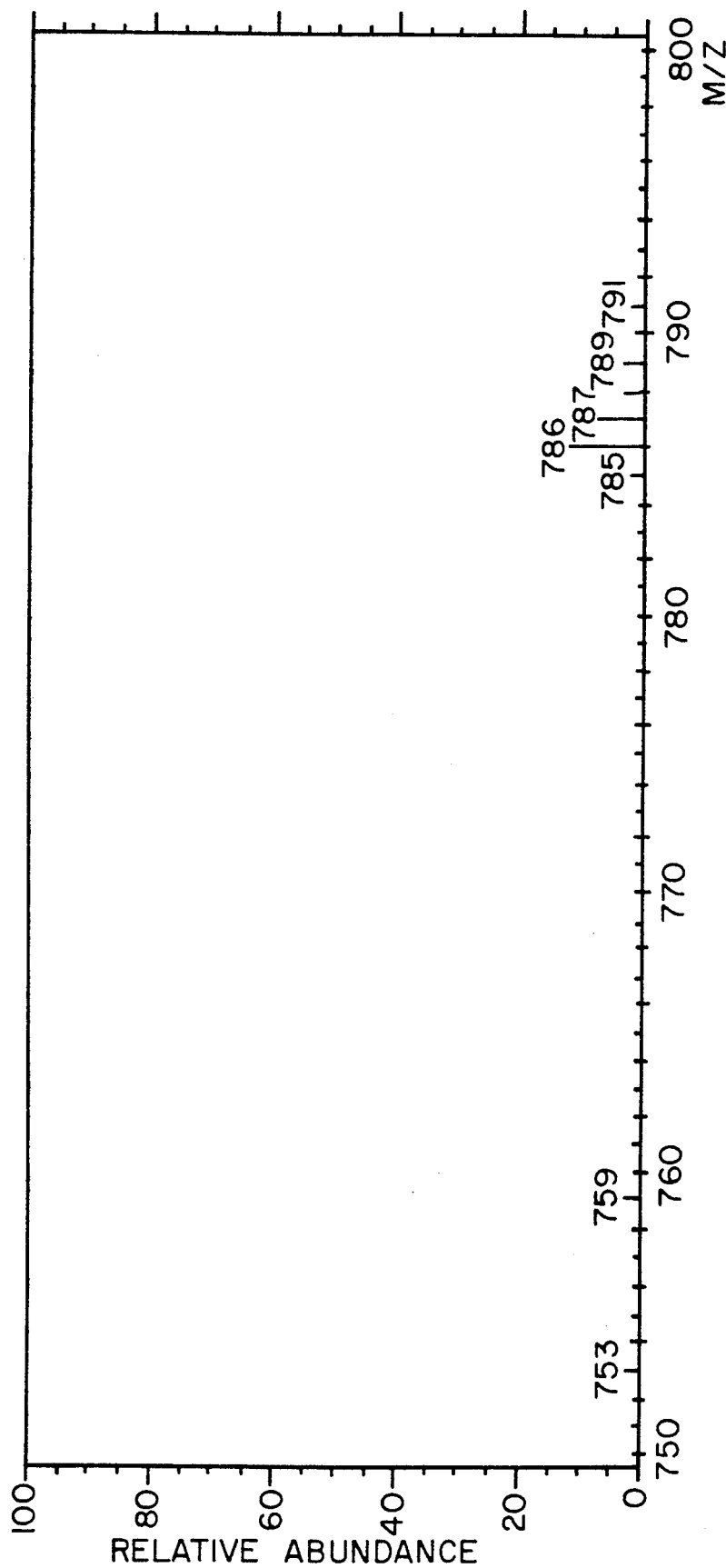

(i) About 20 nmoles of the hexapeptide, Arg-Gly-Tyr-Ala-Leu-Gly, were treated with about 5 μmoles of triethylamine and 5 μmoles of diphenylphosphorylmercaptobenzothiazole in 10 μl of N,N-dimethylformamide for 30 minutes at 50° C. The product mixture was fractionated by reversed phase HPLC. The coupled peptide was recovered as an individual peak and gave a FAB-MS molecularion consistent with the calculated value of 786 amu depicted by FIG. 5.

The coupling reaction is illustrated by Equation 5:

Arg—Gly—Tyr—Ala—Leu—Gly +

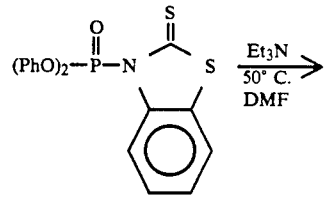

Arg—Gly—Tyr—Ala—Leu—Glycyl—N

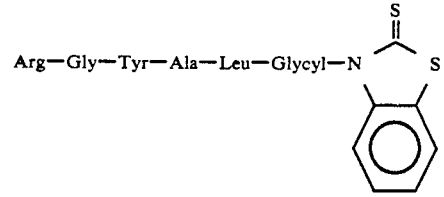

Figure 6:
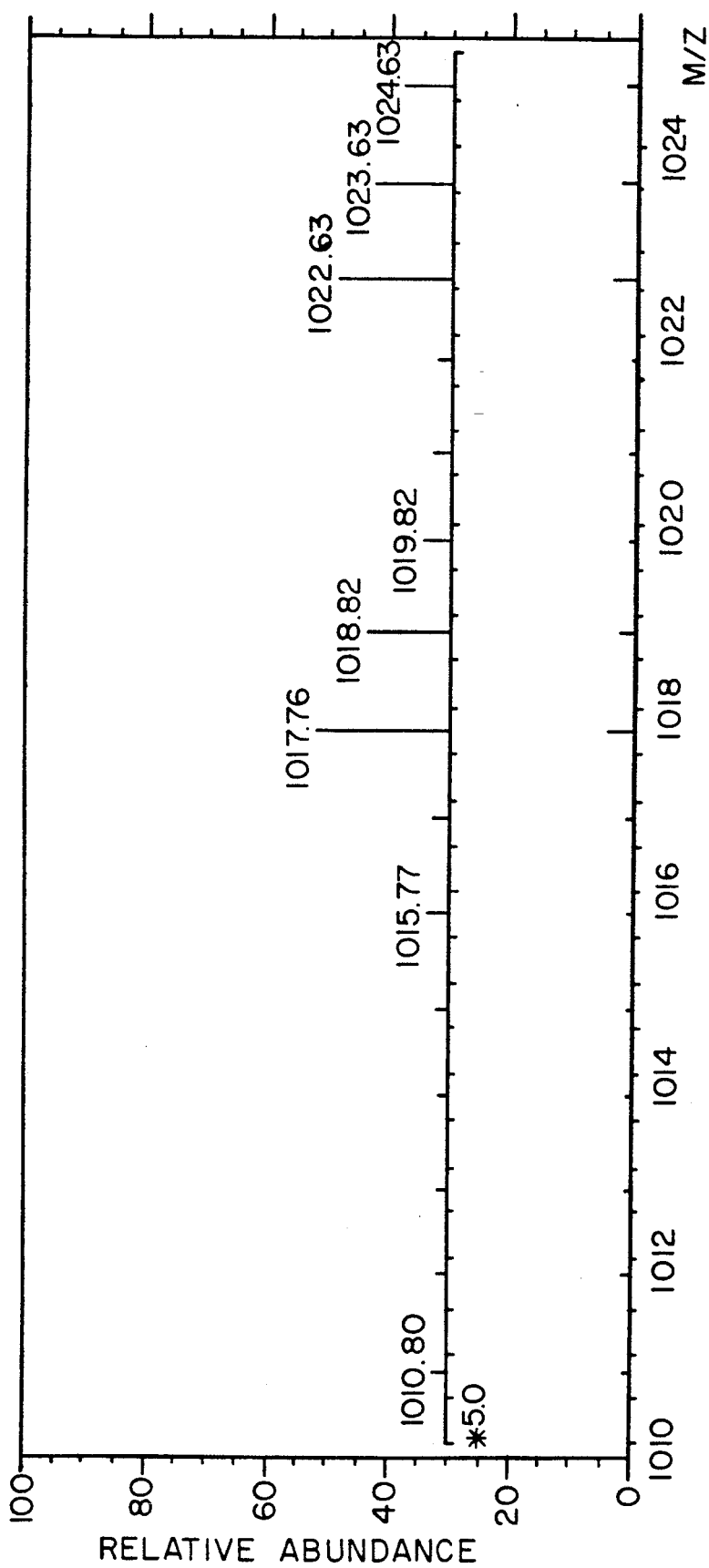

As FIG. 6 shows, a molecular ion of 1018 amu was found after product mixture fractionation when acetonitrile replaced N,N-dimethylformamide as the solvent. The ion is consistent with the diphenylphosphorylpeptidyl mercaptobenzothiazole produced by Equation 6:

Arg—Gly—Tyr—Ala—Leu—Gly +

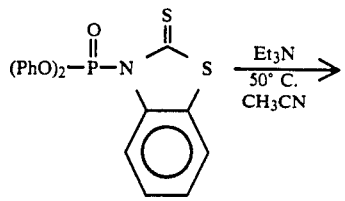

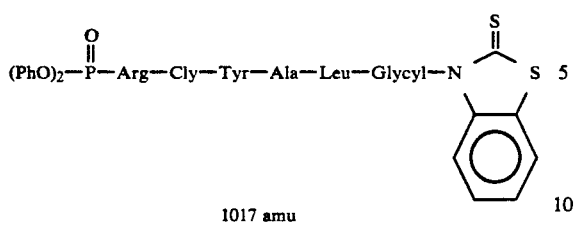

Figure 7:
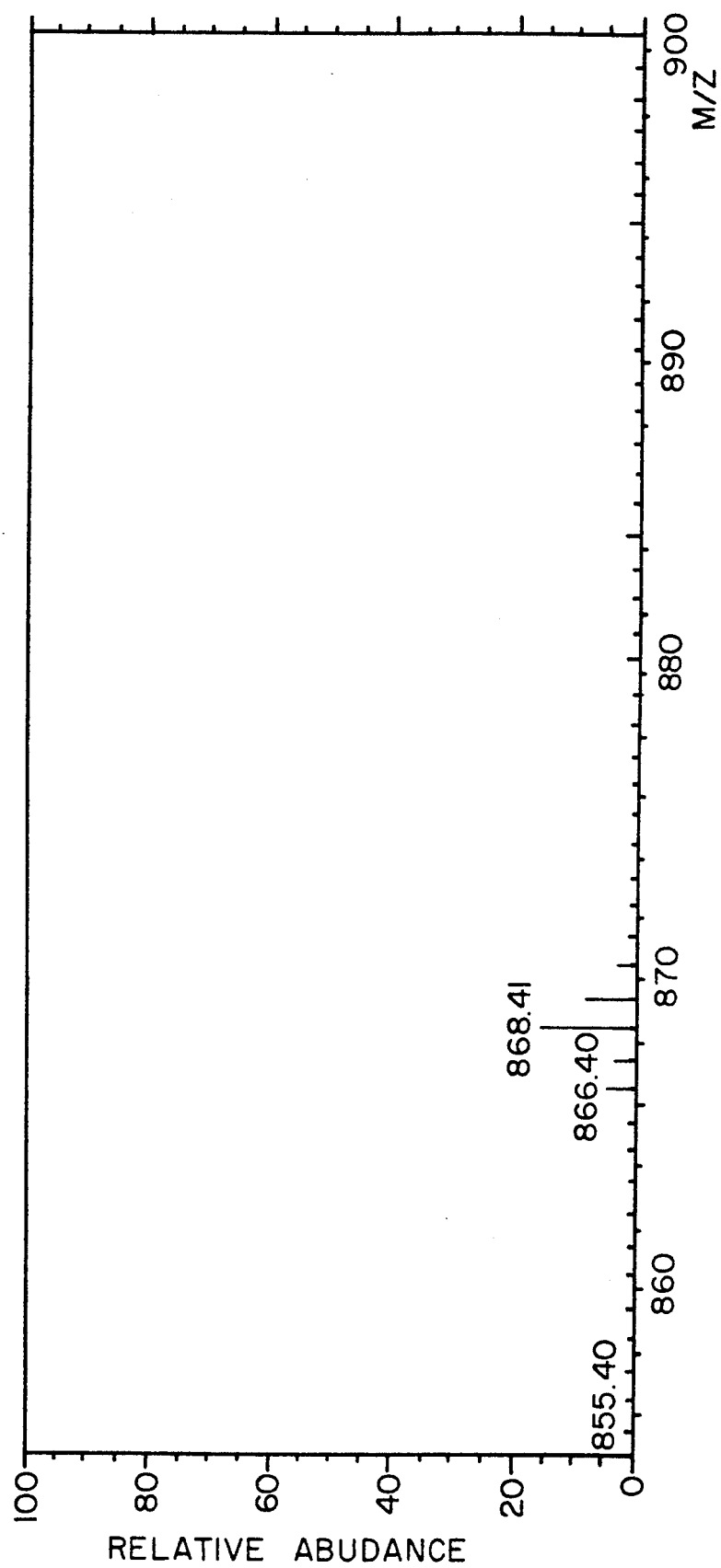

1017 amu (ii) When 20 nmoles of the above hexapeptide were treated with acetic acid and acetic anhydride for 30 minutes at 50° C., a product mixture composed of various acetylated peptides was found by FAB-MS analysis. Subsequent exposure of the mixture to triethylamine in N,N-dimethylformamide yielded a series of azlactone peptides resulting from the elimination of acetic acid at the Glycyl terminus and five-membered ring closure. Subsequent addition of 2-mercaptobenzothiazole (about 5 μmoles) and triethylamine (5 μmoles) in N,N-dimethylformamide for 30 minutes at 50° C. resulted in a product mixture containing acetylated peptidyl mercaptobenzothiazole. As FIG. 7 shows, a molecular ion of 869 amu was found which corresponds to the diacetylated peptidylmercaptobenzothiazole.

This result is consistent with the following reactions collectively identified as Equation 7:

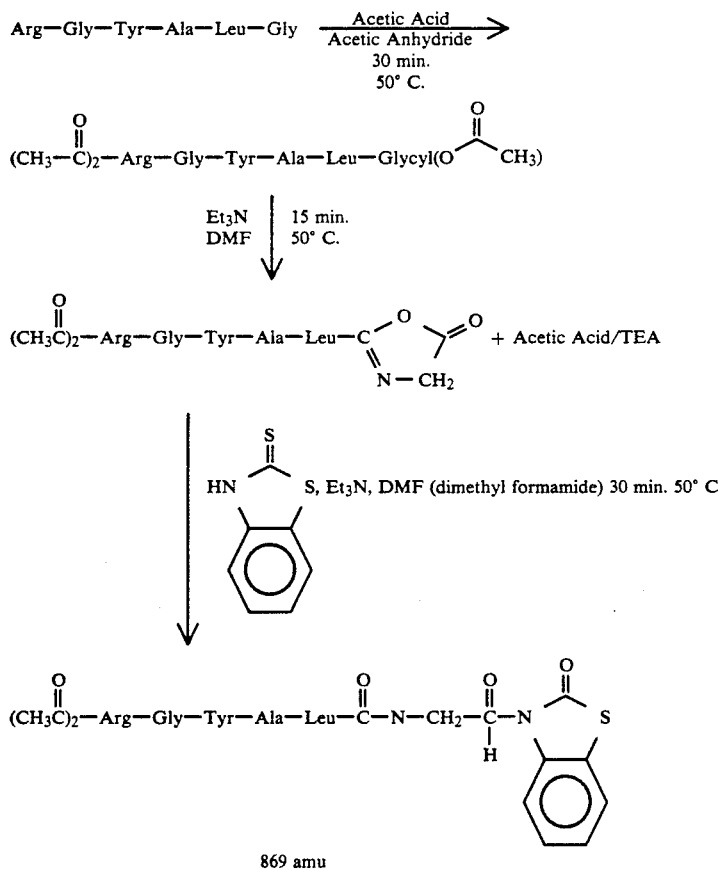

869 amu

The product peptidyl mercaptobenzothiazole may actually exist as the rearranged peptidyl arylthiothydantoins which are not differentiated by mass value.

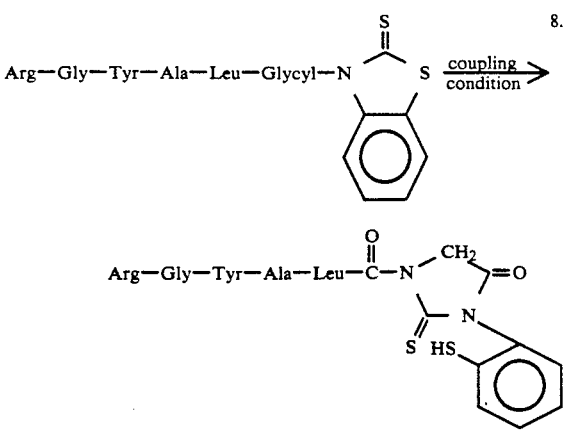

The rearrangement (or cyclization) illustrated by Equation 8 is expected to occur under the basic conditions, e.g., the C-terminal azlactone of the peptide Arg-ly-Tyr-Ala-Leu, of the coupling reaction. Additionally observed FAB-MS ion consistent with cleavage products under the coupling conditions are consistent with the cyclized thiohydantoin peptides. A coupling reaction with compound E would yield the corresponding peptidylaryliminohydantoin.

The Cleavage Reaction

Cleavage may be accomplished in known manner, for example, utilizing acetohydroxamic acid,[6]/a cation exchange resin or concentrated HCL or dilute NaOH as a cleavage reagent.[6]

[6] See, e.g., Stark, G.R. (1968) *Biochemistry* 7:1796.

Acetohydroxamic acid in a basic medium, preferably triethylamine is preferred. The conditions for acetohydroxamate-assisted cleavage of the protein arylthiohydantoin may be varied to include other organic bases, e.g., pyridine, alkyl-, or arylamines, alternate temperatures, solvent systems, and reaction times. The cleavage reagent is utilized in a mixed organic-acqueous solvent system. Other cleavage reagents and solvent systems which may be utilized include thiolates (mercaptide or thiophenoxide) such as thiophenol, 2-mercaptopyridine, N-acylcysteine, or o-acylmercaptoethanol in basic media such as water-acetonitrile with pH greater than 7 adjusted with pyridine, a triakylamine or dilute hydroxide. Dilue triethyl amine in either an organic solvent such as DMF or in aqueous solution may also serve to cleave the peptidyl hydantoin.

The released arylthiohydantoins (or specifically, thiophenoxy- or phenoxy-thiohydantoins) are identified by separation and detection with reversed-phase HPLC techniques.

Equation 9 illustrates a generalized cleavage reaction applied to the protein-thiophenoxythiohydantoin product generated by Equation 3b:

FAB-MS molecular ions at 366 and 325 amu which are consistent with the dipeptide, N-dansylglycylglycine, and the thiophenylthiohydantoin of the C-terminal glycyl residue. The generation of these products is attributed to the peesence of water, not rigorously excluded, from the basic coupling reaction mixture.

The ion detected at 366 amu (see FIG. 4) is consistent with the dansyldiglycine peptide which is, in effect, the cleavage product that would result from a small amount of water present in the reaction mixture, i.e.,

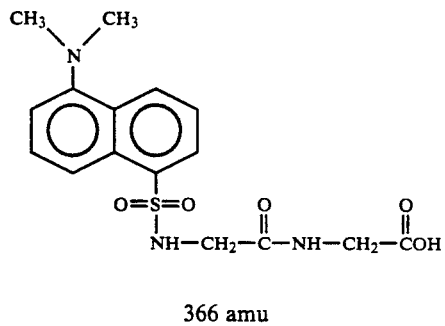

366 amu

The ion detected at 325 amu (see FIG. 4) (control reactions also show background at 325 amu) may be

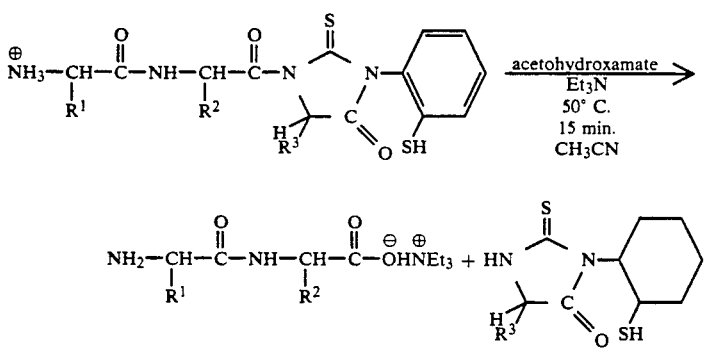

Equation 9

The hydrolytic lability of the coupled peptide to release the arylthiohydantoin was evidenced by the contributed in part by the cleaved thiophenylthiohydantoin, i.e.,

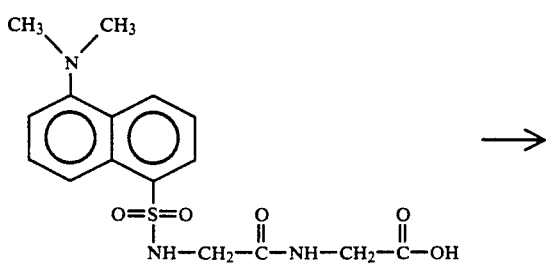

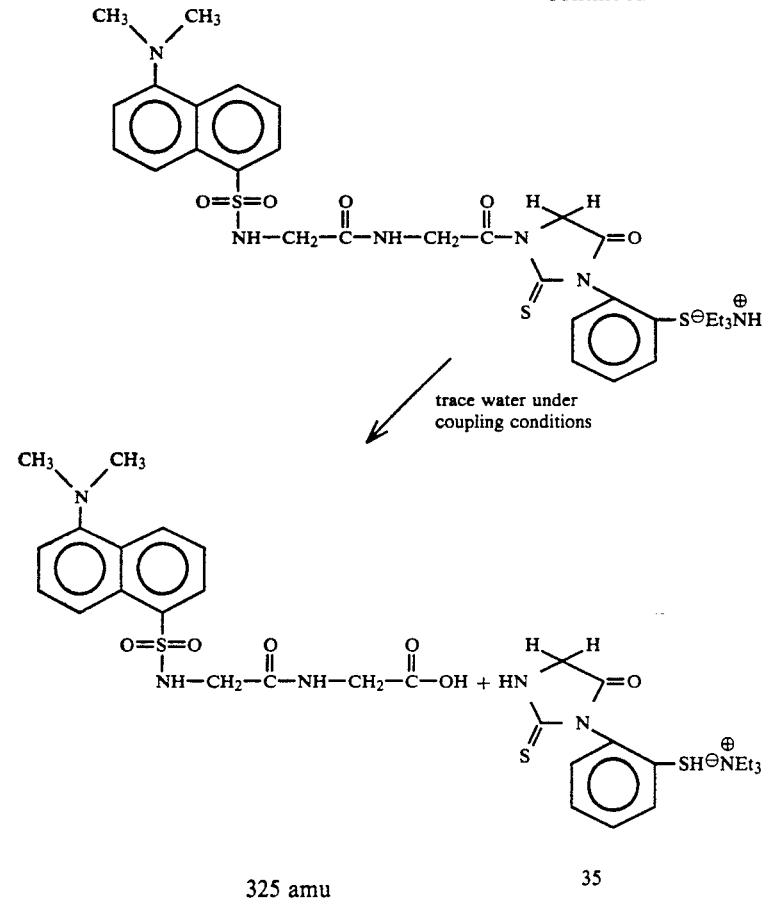

325 amu

The molecular ions tend to exhibit low signal intensity due to the anionic charge borne by triethylamine salt moiety of the products.

The C-terminal sequencing methodology of this invention is applicable to protein and peptide samples of all free carboxylic acids and without preclusive restraint consequent from the chain length of amino acid residue. Sequencing pursuant to the methodology of the invention provides improved sensitivity, speed and yield on sequential degradation cycles. A single cycle of degradation can be accomplished in from about 1 to about 2 hours.

An additional compound H, useful as a carboxyl terminal coupling agent in the sequencing of peptides may be produced pursuant to the following equation:

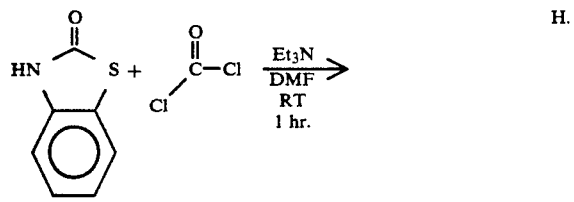

Compound H, albeit not within the scope of Formula I, implicates a free amide moiety

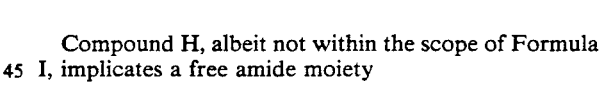

in the coupling reaction as illustrated by the following equation:

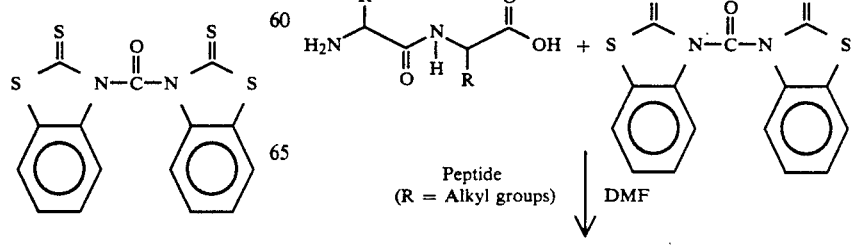

-continued

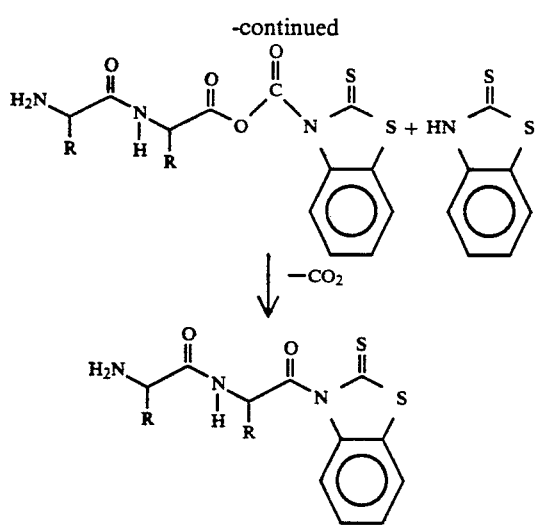

We claim:

1. In a process for the sequential degradation of a peptide which includes reacting the carboxy terminus of said peptide with a coupling reagent to form a peptidyl derivative which is cleavable to provide a derivative of the amino acid residue previously at said carboxy terminus and a peptide lacking such amino acid residue, the improvment which comprises utilizing, as the coupling reagent, a compound of the schematic structural formula:

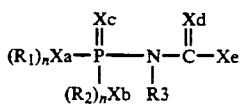

in which

Xa and Xb are O (oxygen), S (sulfur) or N (nitrogen)

$R_1$ and $R_2$ are H, or any alkyl ar aryl radical having not more than about 10 carbon atoms, n is 1 when Xa and Xb are O or S;

n is 2 when Xa or Xb is N when Xa and Xb are both N $(R_1)_n Xa$ and $(R_2)_n Xb$ may be included in an acylic amine or a nitrogen heterocycle;

$R_4$ is an alkyl or aryl radical having not more than about 10 carbon atoms:

Xc is O or S

Xd is O, S or $NR_4$ wherein $R_4$ is H or any alkyl or aryl radical having not more than about 10 carbon atoms Xe is $OR_5$, $SR_5$ or $N(R_5)_2$ wherein $R_5$ is an alkyl or aryl radical having not more than about 12 carbon atoms, and in which

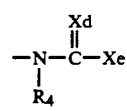

may be included in a ring system

2. A process as defined by claim 1 in which Xd is sulfur.

3. A process as defined by claim 1 in which Xd is oxygen.

4. A process as defined by claims 1, 2, or 3 in which the protein or peptide is activated with acetic anhydride and acetic acid prior to reaction with the coupling reagent.

5. A process as defined by claims 1, 2, or 3 in which the reaction of said carboxy terminus and said coupling agent is effected in the presence of an amine.

6. A process as defined by claims 1, 2, or 3 in which said peptide or protein is immobilized on a solid support prior to said coupling reaction.

7. The coupling reaction product of the carboxyl terminal of a protein or peptide with a compound of Formula I.

8. The coupling reaction product of the carboxyl terminal of a protein or peptide with a compound of formulae A, B, C, or D.

9. The cleavage, or hydrolysis reaction product of the proteinyl or peptidylarylhydantoin, peptidylthiohydantoin or peptidyliminohydantoin prepared by the coupling reaction utilizing a compound of Formula A, B, C, D, E, F or G.

10. The cleavage, or hydrolysis reaction product of the proteinyl or peptidylarylthiohydantoin, peptidylthiohydantoin or peptidylarytiminohydantoin prepared by the coupling reaction utilizing a compound of Formula A.

* * * * *